United States Patent
Hiyama et al.

(10) Patent No.: US 6,269,379 B1
(45) Date of Patent: *Jul. 31, 2001

(54) MEDICAL IMAGE FILING SYSTEM ENABLING REGISTRATION AND RETRIEVAL OF A PLURALITY OF MEDICAL IMAGES

(75) Inventors: Keiichi Hiyama, Akishima; Katsuyoshi Sasagawa, Shirakawa; Atsushi Kazawa, Hachioji, all of (JP)

(73) Assignee: Olympus Optical Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/900,882

(22) Filed: Jul. 25, 1997

Related U.S. Application Data

(63) Continuation of application No. 08/417,832, filed on Apr. 6, 1995, now abandoned.

(30) Foreign Application Priority Data

Apr. 8, 1994 (JP) .................................................. 6-071087

(51) Int. Cl.[7] .................................................. G06F 17/30
(52) U.S. Cl. ......................... 707/104; 358/296; 358/403
(58) Field of Search .................................. 395/601, 615, 395/653; 348/588, 74; 358/403, 296; 382/131, 132, 128; 702/39; 711/120; 345/340; 386/124; 364/521, 200; 707/104; 340/825.31; 435/5

(56) References Cited

U.S. PATENT DOCUMENTS

| | | | |
|---|---|---|---|
| 4,817,050 | * | 3/1989 | Komatsu et al. ..................... 364/900 |
| 4,829,453 | * | 5/1989 | Katsuta et al. ....................... 364/521 |
| 4,958,283 | * | 9/1990 | Tawara et al. ....................... 382/131 |
| 4,962,449 | * | 10/1990 | Schlesinger ......................... 364/200 |
| 5,001,569 | * | 3/1991 | Shigyo ................................. 358/296 |
| 5,027,110 | * | 6/1991 | Chang et al. ........................ 340/731 |
| 5,029,016 | | 7/1991 | Hiyama et al. ...................... 358/403 |
| 5,047,754 | * | 9/1991 | Akatsuka et al. ................... 345/163 |
| 5,111,306 | | 5/1992 | Kanno et al. ........................ 358/403 |
| 5,124,789 | * | 6/1992 | Hiyama et al. ........................ 348/74 |
| 5,187,579 | * | 2/1993 | Hiyama ............................... 348/588 |
| 5,209,220 | * | 5/1993 | Hiyama et al. ...................... 600/109 |
| 5,241,472 | * | 8/1993 | Gur et al. ............................ 382/128 |

(List continued on next page.)

FOREIGN PATENT DOCUMENTS

4212336A * 4/1992 (JP) .

*Primary Examiner*—Thomas Black
*Assistant Examiner*—Charles L. Rones
(74) *Attorney, Agent, or Firm*—Armstrong, Westerman, Hattori, McLeland & Naughton, LLP

(57) ABSTRACT

In an image filing system in accordance with the present invention, image files containing images that should be displayed on a viewing monitor in a conference unit are selected from among retrieved image files using a mouse. A CPU determines how many image files are selected using the mouse and identifies management information contained in the selected image files. Under the control of the CPU, images in a work memory are temporarily stored in an image processor. The images in the image processor are displayed on a retrieval monitor. Management information contained in the selected image files and the number of selected image files are supplied from the CPU to a controller over a bus. Reduced images provided in the form of digital data and contained in the selected image files in the image processor are supplied to a D/A converter under the control of the controller. The D/A converter de-quantizes the digital data into analog data so as to display the reduced images on the viewing monitor.

23 Claims, 14 Drawing Sheets

U.S. PATENT DOCUMENTS

| | | | |
|---|---|---|---|
| 5,245,329 | * | 9/1993 | Gokcebay .................... 340/825.31 |
| 5,276,851 | * | 1/1994 | Thacker et al. .................... 711/120 |
| 5,293,326 | * | 3/1994 | Arima et al. ........................ 702/39 |
| 5,321,520 | * | 6/1994 | Inga et al. .......................... 358/403 |
| 5,361,203 | | 11/1994 | Hiyama et al. ................. 364/413.13 |
| 5,379,757 | * | 1/1995 | Hiyama et al. .................... 600/109 |
| 5,402,788 | * | 4/1995 | Fujio et al. ........................ 600/423 |
| 5,416,602 | * | 5/1995 | Inga et al. .......................... 358/403 |
| 5,440,401 | * | 8/1995 | Parulski et al. .................... 386/124 |
| 5,452,416 | * | 9/1995 | Hilton et al. ...................... 395/161 |
| 5,493,315 | * | 2/1996 | Atchley .............................. 345/516 |
| 5,528,492 | * | 6/1996 | Fukushima .................... 364/419.19 |
| 5,539,426 | * | 7/1996 | Nishikawa et al. ................ 345/115 |
| 5,568,271 | * | 10/1996 | Fukuchi et al. ...................... 386/46 |
| 5,621,429 | * | 4/1997 | Yamaashi et al. ................. 345/340 |
| 5,682,529 | * | 10/1997 | Hendry et al. ..................... 395/653 |
| 5,826,237 | * | 10/1998 | Macrae et al. ......................... 705/2 |
| 5,836,872 | * | 11/1998 | Kenet et al. ........................ 600/306 |
| 5,876,926 | * | 3/1999 | Beecham .............................. 435/5 |

* cited by examiner

FIG.2

| 71 | 72 | 73 | 74 | 75 | 76 | 77 | 78 | 79 | 80 |
|---|---|---|---|---|---|---|---|---|---|
| EXAMI-NATION | SERIAL NUMBER | PATIENT ID | PATIENT NAME | DATE OF EXAMI-NATION | REGION CODE | POSITION CODE | PROCESSOR ID | VIEW IMAGE DATA | REDUCED IMAGE DATA |

| PATIENT ID | PATIENT NAME | DATE OF BIRTH | DATE OF EXAMINATION |
|---|---|---|---|
| 1111 | PATIENT A | 62, 1, 1 | 94, 3, 15 |
| 1111 | PATIENT A | 62, 1, 1 | 94, 3, 16 |
| 1111 | PATIENT A | 63, 1, 1 | 94, 3, 17 |
| 1111 | PATIENT A | 64, 1, 1 | 94, 3, 18 |
| ⋮ | ⋮ | ⋮ | ⋮ |

45a

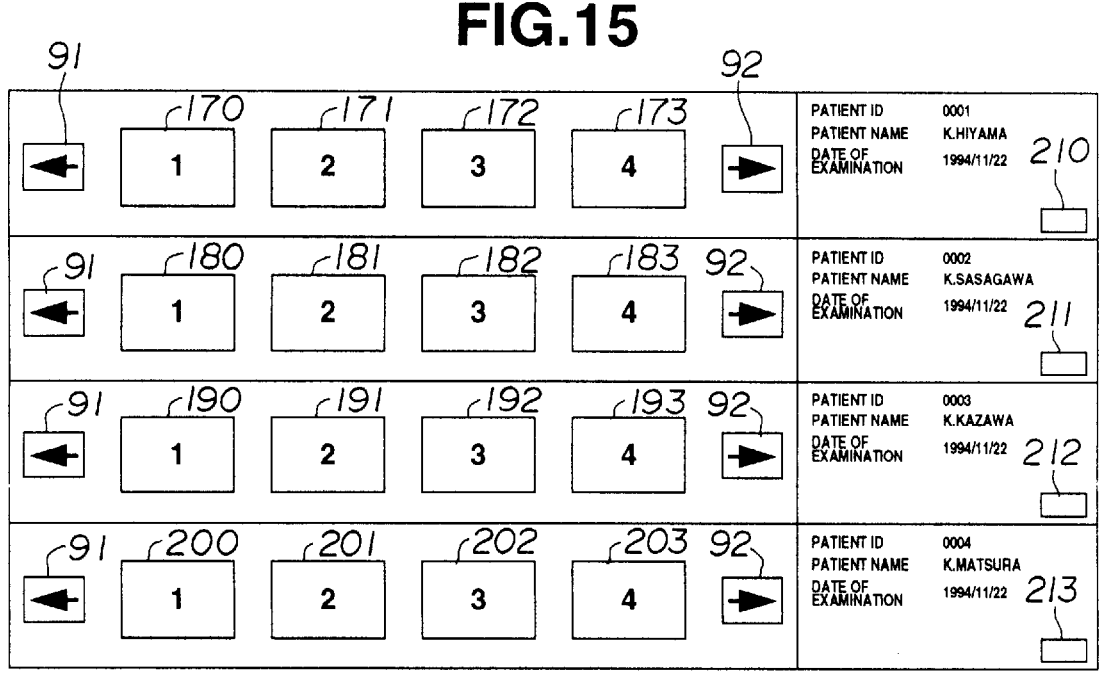

MEDICAL IMAGE FILING SYSTEM ENABLING REGISTRATION AND RETRIEVAL OF A PLURALITY OF MEDICAL IMAGES

This application is a continuation of application Ser. No. 08/417,832 filed Apr. 6, 1995, now abandoned.

BACKGROUND OF THE INVENTION

1. Field of the Invention

The present invention relates to a medical image filing system in which a plurality of medical images are registered or retrieved on or from a medical image database for use in managing numerous images acquired by an endoscope system, diagnostic ultrasound system, or the like.

2. Description of the Related Art

Endoscope systems, in which an elongated insertional part of an endoscope is inserted into a body cavity and a solid-state imaging device or the like is used as an image pickup means, so that intracavitary organs can be examined or diagnosed while being viewed through a monitor screen, have been widely adopted in recent years.

Diagnostic ultrasound systems, in which ultrasonic waves are irradiated to an intracavitary organ and the state of the intracavitary organ is rendered according to the magnitude of reflection or transmission of the ultrasonic waves, so that the intracavitary organ can be examined or diagnosed while being viewed through a monitor screen, have enjoyed popularity these days.

Aside from the endoscope system or diagnostic ultrasound system, diagnostic systems using an electronic (electric) means to enable examination or diagnosis of a living body while viewing the state of the living body have been put to use or proposed.

On the other hand, proposals have been made for an image display unit based on a medical image database that is useful for managing numerous images produced by the endoscope system, diagnostic ultrasound system, or the like.

An image filing system is included in the endoscope system or diagnostic ultrasound system so that endoscopic or ultrasonic images produced by an electronic endoscope or an ultrasound probe can be recorded on a recording medium such as a magneto-optical disk for future diagnostic use, and thus used on a systematic basis.

Prior arts include an image filing system disclosed in, for example, Japanese Patent Laid-Open No.6-110986. The image filing system comprises an image recorder for performing reversible or non-reversible compression on image signals sent from an endoscope system or an ultrasound system and storing the resultant signals as image data representing a plurality of images, an image reproducer for reproducing an image recorded in the image recorder, and a data communication unit enabling communication between an external host computer and the image recorder via a data input/output terminal. Data concerning a patient to be examined by the endoscope or ultrasound system is entered at an examination reception terminal connected to the host computer, transferred to the image recorder via the data communication unit, and then stored in the form of a database. Thus, a great number of images produced by a plurality of endoscope systems or the like can be stored and managed.

An image display unit included in the foregoing image filing system may consist of a processing means for enlarging or reducing at least one first view image without changing the amount of image data, and a synthesizing means for synthesizing a second view image produced by enlarging or reducing the first view image using the processing means and as least the first view image with other image.

The foregoing image display unit can simultaneously display the first view image and the second view image produced by enlarging or reducing the first view image without changing the amount of image data.

However, the image display unit in accordance with the prior art does not allow simultaneous reference of image files containing different retrieval information, for example, endoscopic images rendering a lesion of the same patient and being produced before and after treatment. The operability is unsatisfactory when it comes to close diagnosis to be performed through simultaneous reference of view images retrieved according to different retrieval information.

OBJECTS AND SUMMARY OF THE INVENTION

An object of the present invention is to provide a medical image filing system enabling reference of a plurality of images contained in image files retrieved according to a plurality of retrieval information items and thus realizing close diagnosis.

Another object of the present invention is to provide a medical image filing system making it possible to distinguish a plurality of displayed reduced images according to management information.

Yet another object of the present invention is to provide a medical image filing system that even when the number of reduced images contained in an image file exceeds the number of reduced images to be displayed, enables reference of all the reduced images in the image file.

Still another object of the present invention is to provide a medical image filing system capable of guaranteeing safety of application and other programs to be run.

A medical image filing system in accordance with the present invention comprises an image input means for inputting an image in the form of image data, a file creating means for creating an image file using at least one image and management information concerning the image, a file storage means for storing image files, a file retrieving means for retrieving image files from the file storage means according to the management information, a selecting means for selecting any of the image files retrieved according to the management information by the file retrieving means, and a display means for fetching images from the image files retrieved the data storage means and then selected by the selecting means and displaying them.

Other features and advantages of the present invention will be fully apparent from the description below.

BRIEF DESCRIPTION OF THE DRAWINGS

FIGS. 1 to 19 relate to an embodiment in accordance with the present invention;

FIG. 1 is a block diagram showing the configuration of an image filing system;

FIG. 2 shows the organization of an image file to be retrieved by the image filing system in FIG. 1;

FIG. 3 shows the structure of systems in the image filing system in FIG. 1;

FIG. 4 is a flowchart describing a sequence of system management based on a password and achieved by a password supervisor;

FIG. 5 is a flowchart describing a sequence of image file creation performed by the image filing system in FIG. 1;

FIG. 6 is a flowchart describing a sequence of recording a created image file on a hard disk in a server unit in FIG. 1;

FIG. 7 is a flowchart describing a sequence of retrieving an image file from the hard disk in the server unit in FIG. 1;

FIG. 8 is an explanatory diagram concerning a retrieval monitor displaying a list of image files retrieved according to the sequence of FIG. 7;

FIG. 9 is a flowchart describing a sequence of selecting any of image files retrieved according to the sequence of FIG. 8 and displaying images;

FIG. 10 is an explanatory diagram concerning a screen appearing on the retrieval monitor when one image file is selected according to the sequence of FIG. 9;

FIG. 11 is an explanatory diagram concerning a screen appearing on the retrieval monitor when two image files are selected according to the sequence of FIG. 9;

FIG. 12 is an explanatory diagram concerning a screen appearing on the retrieval monitor when three image files are selected according to the sequence of FIG. 9;

FIG. 13 is an explanatory diagram concerning a screen appearing on the retrieval monitor when four image files are selected according to the sequence of FIG. 9;

FIG. 14 is a flowchart describing patient data editing performed by the image filing system in FIG. 1;

FIG. 15 is an explanatory diagram concerning a screen appearing on the retrieval monitor when four image files are selected by performing editing shown in FIG. 14;

FIG. 16 is an explanatory diagram concerning a screen appearing on the retrieval monitor in edit mode in which the editing described in FIG. 14 is under way;

FIG. 17 is an explanatory diagram concerning an example of a variant screen that appears on a viewing monitor in a conference unit and that renders the contents of image files selected according to the sequence of FIG. 9;

FIG. 18 is an explanatory diagram concerning the viewing monitor in the conference unit which displays in full a desired image contained in an image file selected according to the sequence of FIG. 9; and FIG. 19 is a flowchart describing a sequence of scrolling images contained in image files selected according to the sequence of FIG. 9.

DETAILED DESCRIPTION OF THE PREFERRED EMBODIMENTS

Figure 1:
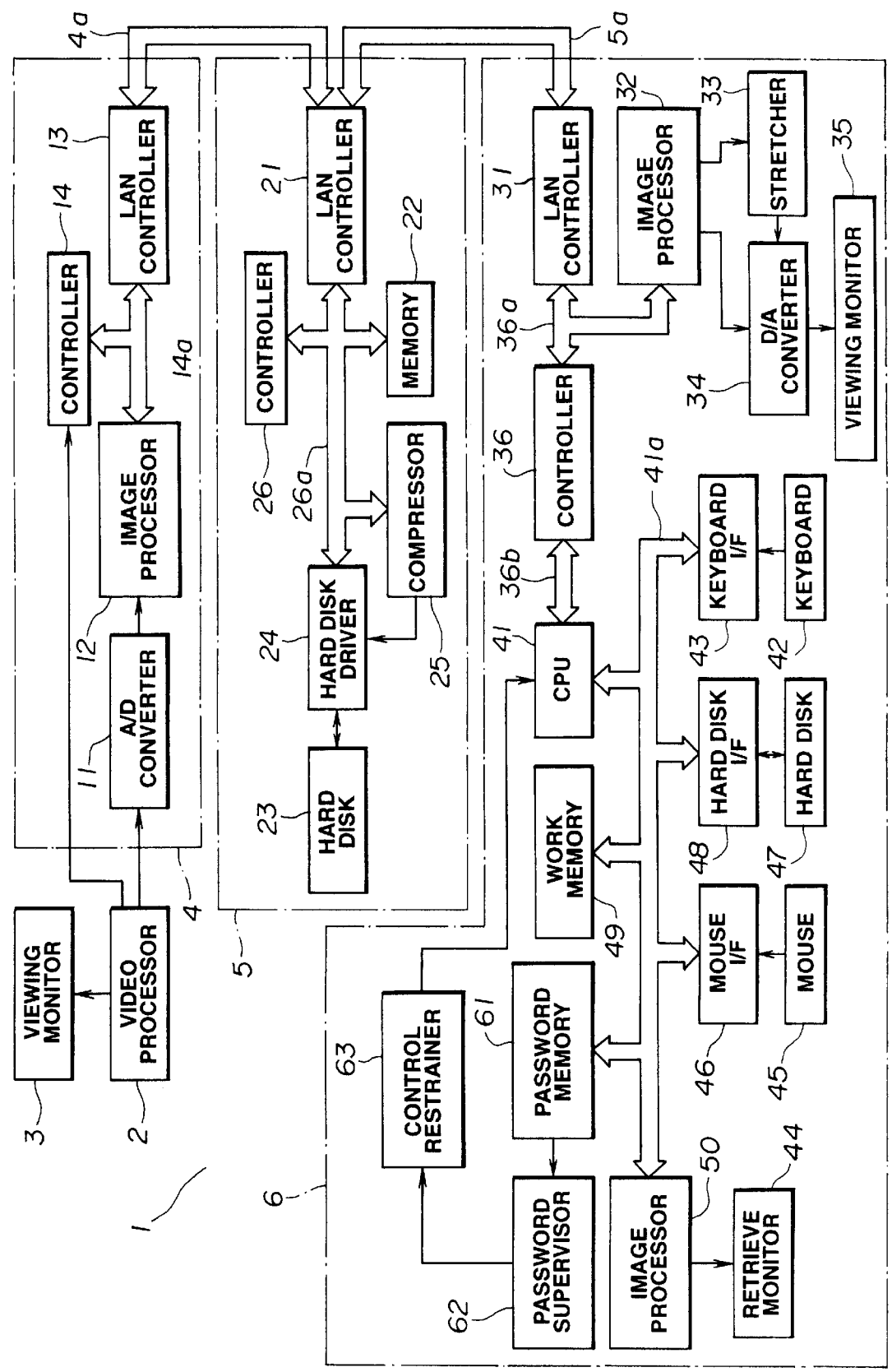

Referring to the drawings, an embodiment of the present invention will be described below.

As shown in FIG. 1, an image filing system 1 of an embodiment in accordance with the present invention comprises a video processor 2 for fetching an image signal from, for example, an electronic endoscope that is not shown and converting it into a video signal, a viewing monitor 3 for rendering the video signal sent from the video processor 2, an input unit 4 for converting the video signal sent from the video processor 2 into an image and performing signal processing on the image, a server unit 5 for storing the image subjected to signal processing by the input unit 4 and compressed an image produced by compressing the image on a reversible or non-reversible basis, and a conference unit 6 for retrieving and displaying the image or compressed image stored in the server unit 5.

The input unit 4 consists of an A/D converter 11 (image input means) for converting R, G, and B analog video signals, which constitute a video signal sent from the video processor 2, into digital signals representing an image, an image processor 12 (file creating means) having a memory for storing images and creating an image file containing management information sent from the video processor 2, a local area network (hereinafter LAN) controller 13 for transmitting an image file created by the image processor 12 to the server unit 5 over a LAN cable 4a, and a controller 14 for transferring management information concerning an image to or from the video processor 2 and controlling the image processor 12 and LAN controller 13.

The video processor 2 has a video signal output terminal, R, G, and B analog video signal output terminals, and a communication signal output terminal. The video signal output terminal is connected to the viewing monitor 3, the R, G, and B analog video signal output terminals are connected to an input terminal of the A/D converter 11, and the communication signal output terminal is connected to the controller 14.

An output terminal of the A/D converter 11 is connected to a data signal terminal of the image processor 12.

A control signal terminal and data signal terminal of the controller 14 are connected to control signal terminals of the image processor 12 and LAN controller 13 over a bus 14a. The controller 14 controls the image processor 12 and LAN controller 13 by sending signals over the bus 14a.

A view provided by, for example, an electronic endoscope that is not shown and converted into a video signal by the video processor 2 is rendered as a view image to be displayed on the viewing monitor 3. When an operator of the video processor 2 determines that the view image should be stored, the video signal is provided in the form of R, G, and B analog video signals to the A/D converter 11. The A/D converter 11 converts the R, G, and B analog video signals into R, G, and B digital video signals by performing given quantization, and supplied them as image data representing a view image to the image processor 12.

The image processor 12 stores the view image supplied from the A/D converter 11 under the control of the controller 14.

The controller 14 performs various data processing including reduction on the view image stored in the image processor 12, appends management information to the view image so as to create an image file, and stores the image file temporarily in the image processor 12 or supplies the image file to the LAN controller 13. When storing an image file subjected to various data processing temporarily in the image processor 12, the controller 14 supplies the image file from the image processor 12 to the LAN controller 13 according to given timing.

The server unit 5 consists of a LAN controller 21 for receiving an image file from the LAN controller 13 in the input unit 4, a memory 22 for temporarily storing the image file received by the LAN controller 21, a hard disk driver 24 for storing the image file received by the LAN controller 21 on a large-capacity storage medium, for example, a hard disk 23 (file storage means), a compressor 25 for compressing the image file received by the LAN controller 21 on a reversible or non-reversible basis and sending a compressed image to the hard disk driver 24, and a controller 26 for controlling the LAN controller 21, memory 22, hard disk driver 24, and compressor 25. The hard disk driver 24 stores an image file and compressed image on the hard disk 23, and the LAN controller 21 transmits the image file or compressed image stored on the hard disk 23 to the conference unit 6 over a LAN cable 5a.

A LAN cable terminal 4a of the LAN controller 13 in the input unit 4 is connected to the LAN controller 21 in the server unit 5. The LAN cable 4a is what is called a 10-base-T cable, wherein a twisted pair is used to enable bidirectional data communication at a data transfer rate of 10M bits/sec within a length of 100 mm and to thus permit control and data transfer among a plurality of units.

A control signal terminal and data signal terminal of the controller 26 in the server unit 5 are connected to control signal terminals of the memory 22, LAN controller 21, and hard disk driver 24 over a bus 26a.

In the server unit 5, the LAN controller 21 receives an image file from the LAN controller 13 in the input unit 4 over the LAN cable 4a. The controller 26 stores the image file received by the LAN controller 21 temporarily in the memory 22. The hard disk driver 24 stores the image file on, for example, the hard disk 23.

The conference unit 6 consists of a LAN controller 31 for receiving an image file or compressed image from the LAN controller 21 in the server unit 5 over a LAN cable 5a, an image processor 32 (data memory means) for storing the image file or compressed image received by the LAN controller 31, a stretcher 33 for stretching the compressed image stored in the image processor 32, a D/A converter 34 for converting an image represented by digital signals and contained in the image file stored in the image processor 32 and the image stretched by the stretcher 33 into R, G, and B analog video signals by performing de-quantization, a viewing monitor 35 (display means) for rendering the R, G, and B analog video signals provided by the D/A converter 34, and a controller 36 for controlling the image processor 32.

A data signal terminal of the image processor 32 is connected to an input terminal of the D/A converter 34. An output terminal of the D/A converter 34 is connected to the viewing monitor 35. A control signal terminal and data signal terminal of the controller 36 are connected to control signal terminals of the image processor 32 and LAN controller 31 over a bus 36a. The control signal terminal and data signal terminal of the controller 36 are connected to a control signal terminal of a CPU 41, which will be described later, over a bus 36b.

The conference unit 6 further comprises a CPU 41 (file retrieving means) for controlling the controller 36, a keyboard 42 for use in entering a request for retrieving an image file to be issued to the server unit 5 and entering various information concerning the image file, a keyboard interface 43 for attaining consistency between a signal sent from the keyboard 42 and a signal sent from the CPU 41, a retrieval monitor 44 for displaying information entered at the keyboard 42, a mouse 45 (selecting means) for use in giving an instruction to change coordinates of a cursor in a screen on the retrieval monitor 44 into any other coordinates, a mouse interface 46 for attaining consistency between a signal sent from the mouse 45 and a signal sent from the CPU 41, a hard disk 47 storing programs to be run by the CPU 41 and various data including the image data representing a menu screen on the retrieval monitor 44, a hard disk interface 48 for attaining consistency between a signal sent from the hard disk 47 and a signal sent from the CPU 41, a work memory 49 used as a work area by the CPU 41 during various processing, and an image processor 50 including a memory for storing R, G, and B digital video signals to be rendered on the retrieval monitor 44.

The conference unit 6 further comprises a password memory 61 for storing a password included in information entered at the keyboard 42 and transferred by the CPU 41, a password supervisor 62 for determining what level the password stored in the password memory 61 ranks, and a control restrainer 63 for restraining control of the CPU 41 according to the result of determination made by the password supervisor 62.

A control signal terminal and data signal terminal of the CPU 41 are connected to control signal terminals and data signal terminals of the hard disk interface 48, mouse interface 46, keyboard interface 43, work memory 49, image processor 50, and password memory 61 over a bus 41a. The CPU 41 controls the hard disk interface 48, mouse interface 46, keyboard interface 43, and work memory 49 over the bus 41a.

The mouse interface 46 detects a signal having a value that corresponds to a magnitude of physical relative movement of the mouse 45, and places the signal in the work memory 49. The work memory 49 stores the magnitude of movement.

The keyboard interface 43 places a character information signal supplied from the keyboard 42 in the work memory 49. The work memory 49 stores the character information or the like.

The hard disk interface 48 reads programs to be run by the CPU 41 and image data representing a menu screen of the retrieval monitor 44 from the hard disk 47, places the read programs and image data in the work memory 49. The work memory 49 stores the programs and the image data for the retrieval monitor 44.

The CPU 41 loads programs from the hard disk 47 to the work memory 49 at the time of turning on the power supply, and runs the programs to make actions.

As mentioned above, an image file stored on the hard disk 23 in the server unit 5 is supplied to the hard disk driver 24 under the control of the controller 26, and then temporarily stored in the memory 22 or supplied directly to the LAN controller 21. The image file is fed from the LAN controller 21 to the LAN controller 31 in the conference unit 6 over the LAN cable 5a.

In the conference unit 6, the LAN controller 31 supplies an image file to the image processor 32 under the control of the controller 36. The image file read from the hard disk 23 in the server unit 5 and then stored in the image processor 32 is divided into a view image represented by digital data and management information under the control of the controller 36. The view image represented by digital data is stored in the image processor 32, while the management information is sent to the CPU 41 over the bus 36b.

The image processor 32 stores the view image. The view image stored in the form of digital signals in the image processor 32 is converted into R, G, and B analog video signals by the D/A converter 34 through de-quantization, and then supplied to the viewing monitor 35. The viewing monitor 35 renders the supplied R, G, and B analog video signals. When the view image is a compressed image, the view image is stretched by the stretcher 33 and then supplied to the D/A converter 34.

The CPU 41 performs computation so that a cursor moved by the mouse 45, character information entered at the keyboard 42, image data representing a menu screen or the like on the retrieval monitor 44 and being retrieved from the hard disk 47, and management information can be displayed in a synthetic or individual fashion, and stores them as image data in the image processor 50.

The file organization of an image file containing view image management information will be described in conjunction with FIG. 2. As shown in FIG. 2, management information consists of an examination identification (hereinafter ID) number 71 assigned to each examination during which a plurality of consecutive images are stored, an image serial number 72 starting with 1 and indicating how many images are stored prior to an image concerned during the examination indicated with the ID number 71, a patient ID number 73, a patient name 74, a date of examination 75, a region code indicating a region to be examined in a human body, a position code 77 indicating a detailed position of the region to be examined in a human body, and an ID number 78 of the video processor 2. An image file consists of the above management information, a view image 79 provided in the form of view image data, and reduced images 80 of the view image regarded as index images and provided in the form of reduced image data.

The view image data contained in an image file stored on the hard disk 23 is composed of a given number of bytes resulting from quantization to be performed so that, for example, a color view image is segmented into a matrix of 640 dots sideways by 480 dots lengthwise, and levels of each of R, G, and B signals rendering each dot are represented using, for example, eight bits.

The reduced image data contained in an image file stored on the hard disk 23 is composed of a given number of bytes resulting from quantization to be performed so that a color view image is segmented into a matrix of 160 dots, which is a quarter of 640 dots, sideways and 120 dots, which is a quarter of 480 dots, lengthwise, and then levels of each of R, G, and B signals rendering each dot are represented using, for example, eight bits.

Next, mention will be made of the role of a password in system management under an operating system in the conference unit 6, especially, in system maintenance such as version upgrading of an application system.

In the conference unit 6, the CPU 41 transfers a password entered at the keyboard 42 to the password memory 61. The password supervisor 72 fetches the password from the password memory 61 and determines whether the password ranks level 1.

The password supervisor 72 transfers a result of determination to the control restrainer 63. In response to the result of determination, the control restrainer 62 restrains control of the CPU 41.

A password may not be entered at a keyboard but may be entered using a bar code reader, magnetic card reader, mouse, or touch-sensitive panel.

Figure 3:
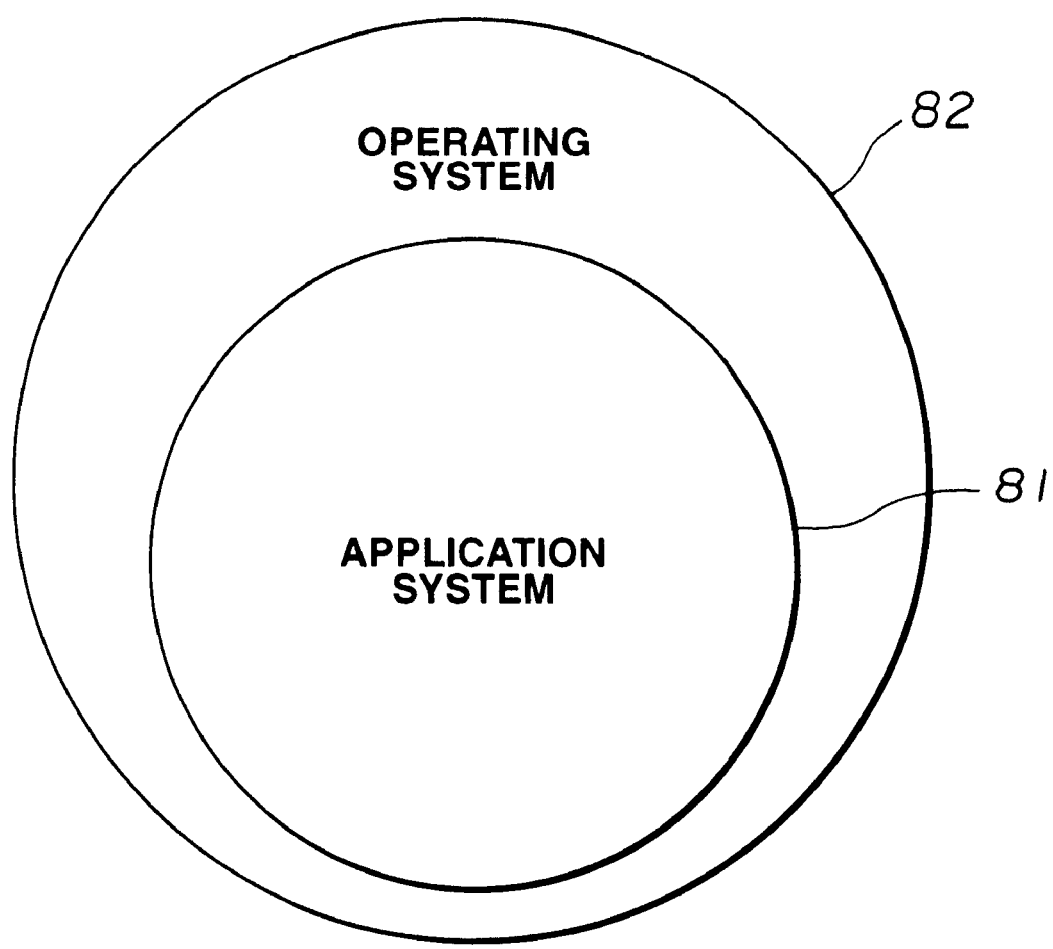
Figure 4:
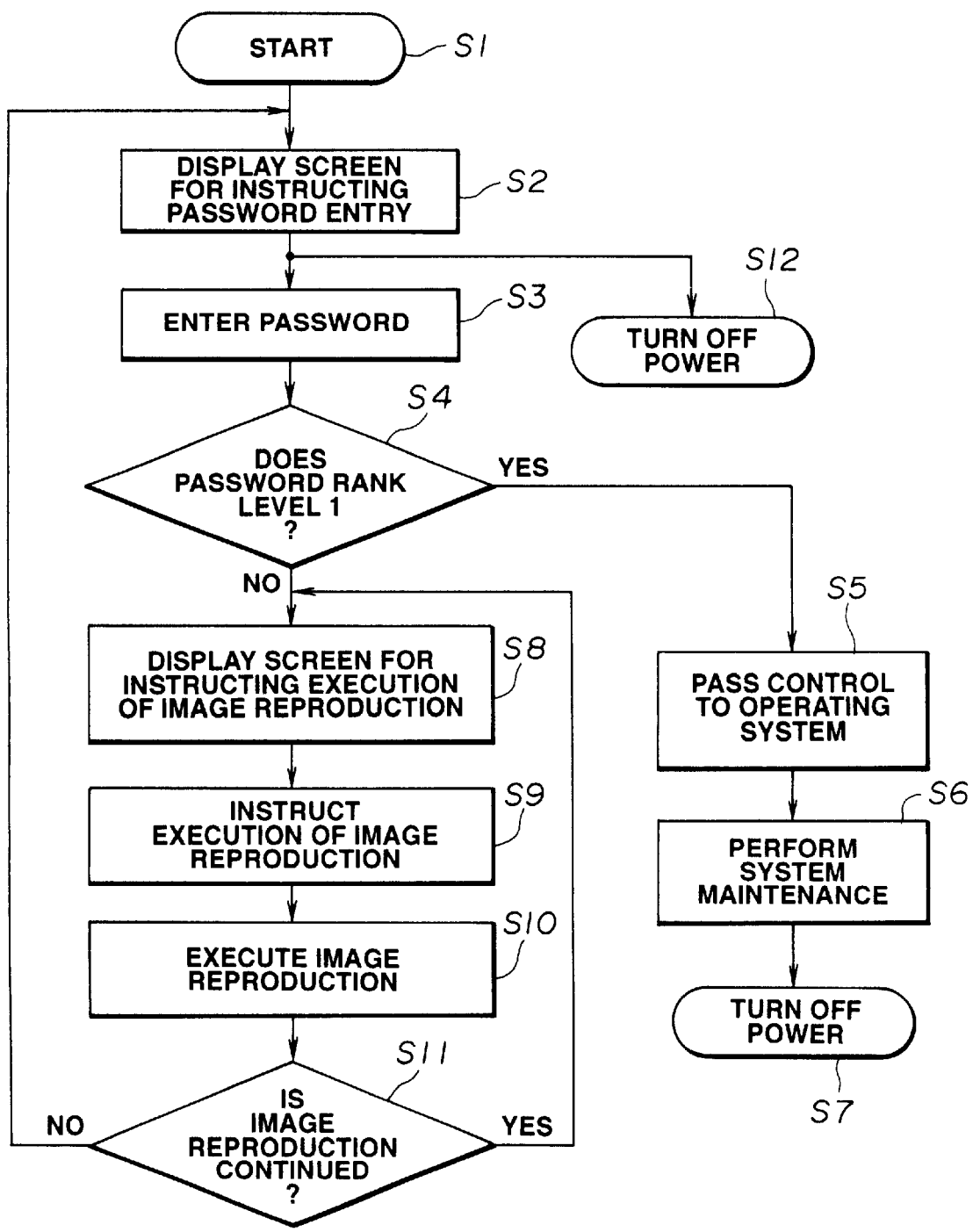

In the conference unit 6, as shown in FIG. 3, an application system 81 activates programs responsible for control of image reproduction. The application system 81 runs under an operating system 82.

During system management performed under the operating system 82, as shown in FIG. 3, an operator turns on the power supply of the conference unit 6 at step S1. The CPU 41 gives a password entry instruction through the retrieval monitor 44 at step S2. When a password is entered at the keyboard 42 at step S3, the password is transferred to the password memory 61. The password is thus stored in the password memory 71.

At step S4, the password supervisor 62 fetches the password from the password memory 61 and determines whether the password ranks, for example, level 1. If the password ranks level 1, a flag in the password supervisor 62 is set as listed in Table 1. The value 1 is transferred to the control restrainer 63. The control restrainer 63 transfers data to permit the CPU 41 to pass control to the operating system 82. Control is then passed to step S5.

TABLE 1

| | Flag |
|---|---|
| Level 1 | 1 |
| Other than level 1 | 0 |

At step S5, the CPU 41 passes control from a program, which runs under the application system 81 so as to control image reproduction, to the operating system 82. The CPU 41 then displays an image concerning the operating system 82 on the retrieval monitor 44, and passes control to step S6. At step S6, the operating system 82 can be operated using the keyboard 42 or the like. The operating system 82 can execute system maintenance to copy files or update programs or can run programs other than the program for controlling image reproduction. For terminating system maintenance, the power supply is turned off at step S7. This causes the operating system 82 to terminate.

If it is determined at step S4 that the password does not rank level 1, the flag in the password supervisor 62 is reset as listed in Table 1. The value 0 is transferred to the control restrainer 63. The control restrainer 63 transfers data to disable the CPU 41 from passing control to the operating system 82. Control is then passed to step S8.

At step S8, the CPU 41 instructs the retrieval monitor 44 to display, for example, a menu screen in which a program for controlling an image can run under the application system 81 and execution of image reproduction can be instructed.

When an instruction is entered at the keyboard 42 at step S9, image reproduction is executed at step S10. For example, the CPU 41 controls the controller 36 so that an image will be fetched from the server unit 5, reproduced, and sent to and displayed on the viewing monitor 35.

At step S10, when the image fetched from the server unit 5 is an image compressed on a reversible or non-reversible basis, the CPU 41 transfers the image to the stretcher 33, and sends a stretched image to the viewing monitor 35. The stretched image is then displayed.

The CPU 41 then checks if image reproduction terminates. At step S11, whether or not to continue reproduction is indicated on the retrieval monitor 44. For example, when it is designated at step S11 that modification of patient records or storing of modified patient records in the server unit 5 will be continued (when the result of determination made at step S11 is in the affirmative), control is passed to step S8 at which a screen for instructing execution of image reproduction, for example, a menu screen is displayed.

When it is designated at step S11 that image reproduction is not be continued (the result of determination made at step S11 is in the negative), control is returned to step S2 at which a screen for instructing entry of a password is displayed. When the power supply is turned off at step S12, the application system 81 terminates.

When a password is used for system management, unless a password ranking level 1 is entered, an operator cannot run the operating system 82. This restraint guarantees safety of running application and other programs.

Owing to the restraint provided by a password, a third person is disabled from copying a file under the operating system 82. Consequently, invasion of computer virus into a running application or other program can be prevented.

System management may not be based on a password. Alternatively, the conference unit 6 may be provided with, for example, a keyhole into which a key is fitted in order to close a lock and a key and lock supervisor for supervising the lock closed with the key. System management based on this mechanism would have the same advantage as the system management based on a password.

The operation of the image filing system 1 having the aforesaid configuration will be described.

A view provided by, for example, an electronic endoscope and converted into a video signal by the video processor 2 is rendered as a view image through the viewing monitor 3. When an operator of the video processor 2 determines that the view image should be recorded, the view image is supplied in the form of R, G, and B analog video signals to the A/D converter 11, converted into R, G, and B digital video signals by the A/D converter 11, supplied in the form of view image data to the image processor 12, and then stored in the image processor 12.

The video processor 2 supplies management information concerning a view image and having been entered by an operator before or during examination to the controller 14 over a communication line.

The controller 14 performs various data processing including reduction on the view image recorded in the image processor 12, and temporarily stores the view image with the management information appended as an image file in the image processor 12 or supplies the image file to the LAN controller 13. After temporarily storing the image file having undergone the various data processing in the image processor 12, the controller 14 transfers the view image from the image processor 12 to the LAN controller 13 according to given timing.

The controller 14 controls the image processor 12 and LAN controller 13 using signals sent over the bus 14a.

Figure 5:
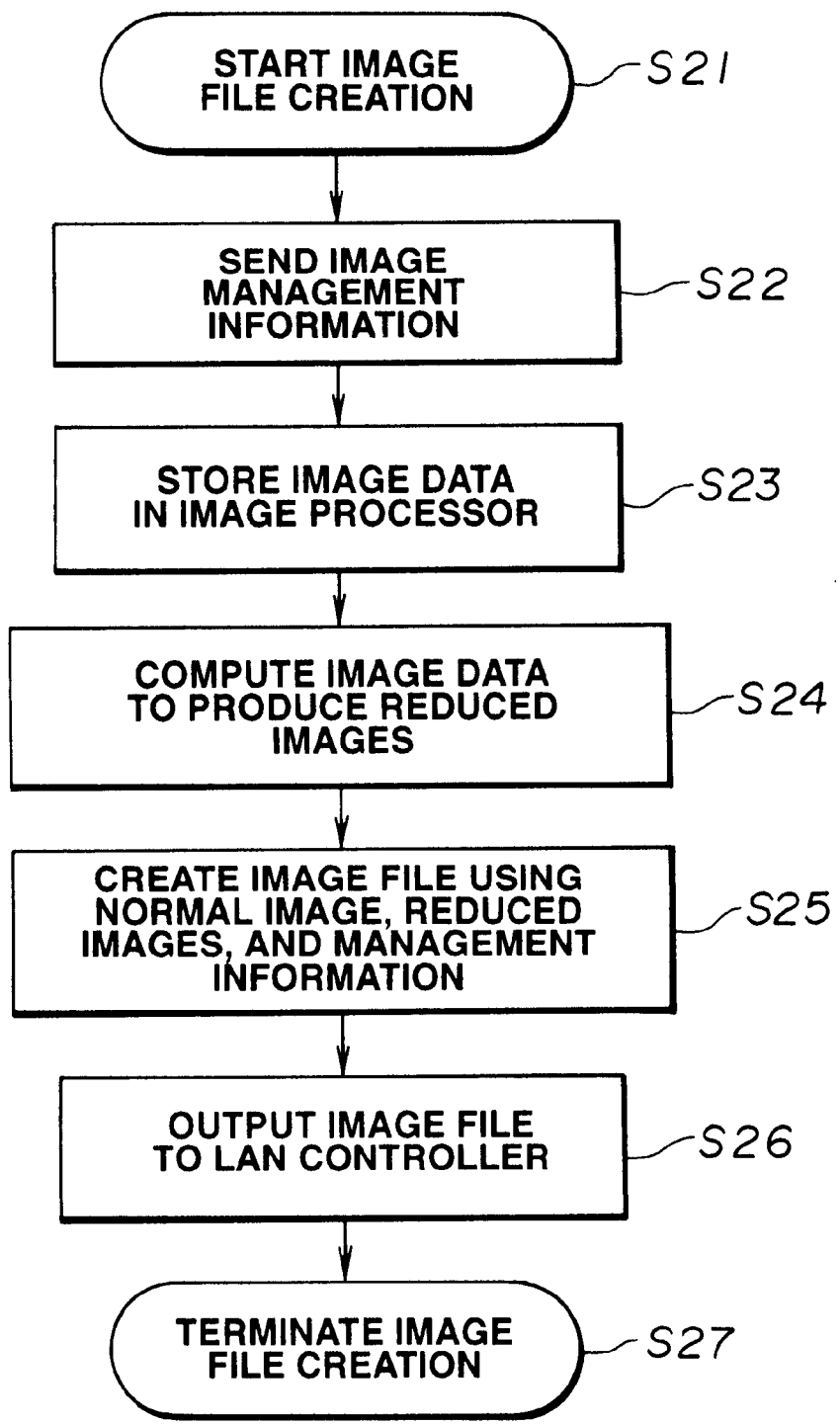

Next, a sequence followed by the controller 14 will be described in conjunction with FIG. 5.

When an operator of the video processor 2 determines that a view image should be recorded, a sequence starts with step S21. Management information concerning the view image is sent to the controller 14 at step S22. The view image is stored in the form of view image data in the image processor 12 at step S23.

The controller 14 performs computation to convert the view image stored in the image processor 12 into reduced images. Management information is appended to the view image and reduced images, thus creating an image file. The image file is temporarily stored in the image processor 12 or supplied to the LAN controller 13. At step S26, the created image file is sent from the LAN controller 13 to the LAN controller 21 in the server unit 5 over the LAN cable 4a. The sequence terminates at step S27.

The image file fed to the LAN controller 21 in the server unit 5 is placed temporarily in the memory 22 under the control of the controller 26. With the control of the controller 26, the image file in the memory 22 is saved on the hard disk 23 that is a large-capacity storage medium via the hard disk driver 24.

Next, a sequence followed by the controller 26 will be described in conjunction with FIG. 6.

When an image file is fed to the LAN controller 21, a sequence starts with step S31. The image file is placed in the memory 22 at step S32.

The controller 26 saves the image file placed in the memory 22 onto the hard disk 23 via the hard disk driver 24 at step S33, and terminates the sequence at step S34.

The CPU 41 in the conference unit 6 controls, as shown in FIG. 1, the hard disk interface 48, mouse interface 46, keyboard interface 43, image processor 50, work memory 49, and password memory 61 over the bus 41a.

The CPU 41 passes control as mentioned above so that the hard disk interface 48 will read a program equivalent to processing executed by the CPU 41 from the hard disk 47.

The read program is run to execute reproduction in which image files recorded on the hard disk 23 in the server unit 5 are retrieved and images contained in the image files are displayed on the viewing monitor 35 in the conference unit 6.

Next, retrieval to be executed in the image filing system 1 by running a read program will be described in conjunction with FIG. 7.

Figure 7:
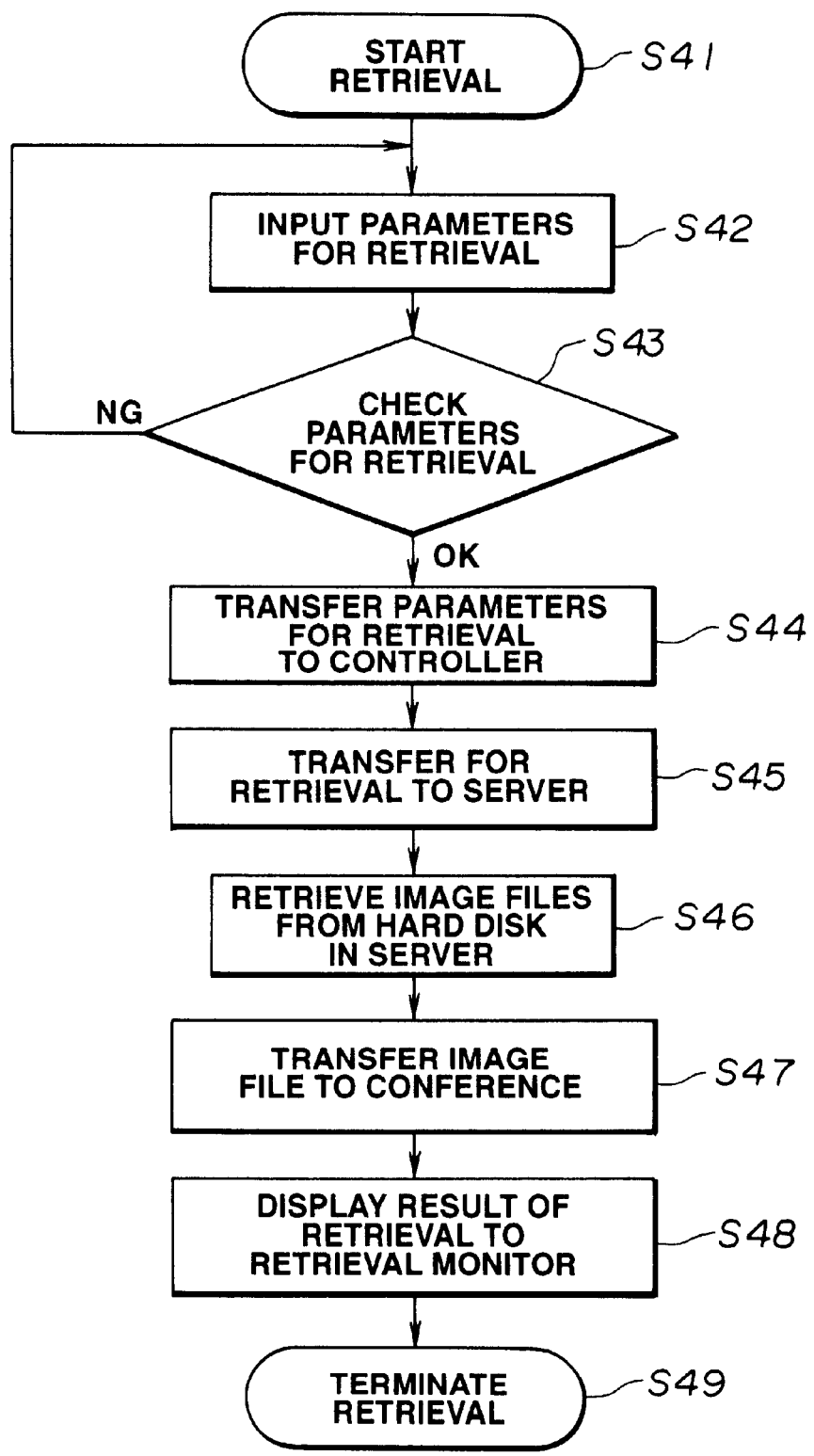

As shown in FIG. 7, retrieval starts with step S41. At step S42, parameters for retrieving an image file are entered at the keyboard 42. It is checked at step S43 if the parameters for retrieval are satisfactory. If it is found at step S43 that the parameters for retrieval satisfy an operator, control is passed to step S44. If the parameters for retrieval do not satisfy the operator, control is returned to step S42. The parameters for retrieval are modified by, for example, adding another parameters.

When entry of the parameters for retrieval is completed, at step S44, the parameters for retrieval entered at step S42 are delivered to the controller 35 over the bus 36b. At step S45, the LAN controller 31 is controlled by the controller 36 over the bus 36a. The parameters for retrieval are sent to the LAN controller 21 in the server unit 5 over the LAN cable 5a, and temporarily placed in the memory 22 by the controller 26 in the server unit 5.

At step S46, the controller 26 controls the LAN controller 21, memory 22, and hard disk driver 24 over the bus 26a, and attempts to retrieve image files from the hard disk 23 according to the parameters for retrieval placed in the memory 22. If image files defined with the parameters for retrieval are found, the image files are temporarily placed in the memory 22.

At step S47, the image files in the memory 22 are supplied to the LAN controller 21 under the control of the controller 26. The LAN controller 21 sends the image files to the LAN controller 31 in the conference unit 6 over the LAN cable 5a under the control of the controller 26. With the control of the controller 36, the image files are temporarily stored in the image processor 32. Thereafter, management information concerning the image files are sent to the CPU 41 over the bus 36b and then placed temporarily in the work memory 49 under the control of the CPU 41.

At step S48, the management information placed in the work memory 49 is transferred to the image processor 50 under the control of the CPU 41. The image processor 50 runs a program to convert the whole or part of the management information into a screen, and displays the screen on the retrieval monitor 44. Retrieval terminals at step S49.

Figures 6, 8:
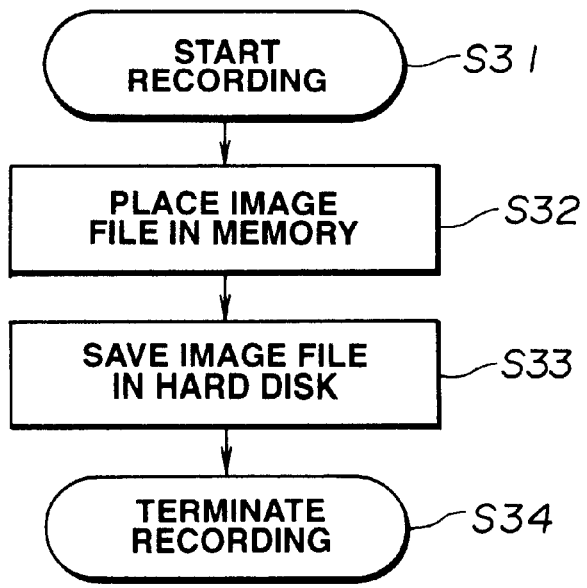

FIG. 8 shows a screen appearing on the retrieval monitor 44 at the termination of retrieval performed according to the parameters for retrieval specifying endoscopic images of patient A.

As shown in FIG. 8, a cursor 45a whose display position (coordinates) is changeable by moving the mouse 45 is displayed on the retrieval monitor 44.

Displaying of reduced images contained in image files retrieved as mentioned previously will be described in conjunction with FIG. 9.

Figure 9:
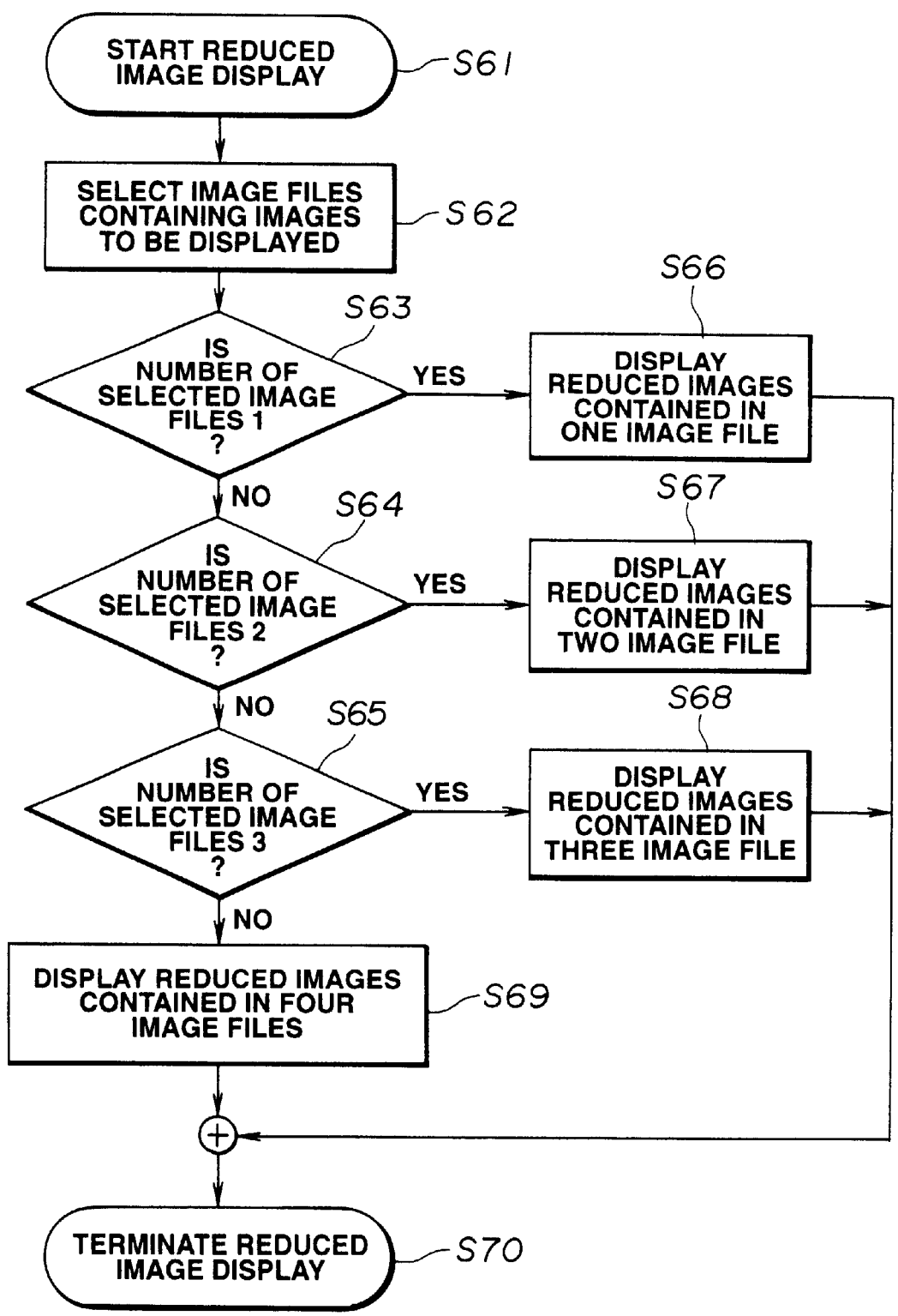

As shown in FIG. 9, displaying of reduced images that are retrieved index images starts with step S61. At step S62, image files containing images that should be displayed on the viewing monitor 35 in the conference unit 6 are selected from among retrieved image files. This selection is achieved by moving the mouse 45 to the item of each intended image file as shown in FIG. 8 and then clicking a button on the mouse 45.

At step S63, S64, and S65, the CPU 41 determines how many image files are selected using the mouse 45 and identifies management information in the selected image files. In this embodiment, the number of image files that can be selected simultaneously ranges from 1 to 4.

When determination is made at step S63, S64, or S65, at step S66, S67, S68, or S69, images read from the work memory 49 are temporarily stored in the image processor 50 under the control of the CPU 41, and then displayed on the retrieval monitor 44.

At step S66, S67, S68, or S69, the management information in the selected image files and the number of selected image files are sent to the controller 36 over the bus 36b. Under the control of the controller 36, reduced images provided in the form of digital data and contained in selected image files in the image processor 32 are supplied to the D/A converter 34. The D/A converter 35 de-quantizes the digital data representing the reduced images to produce analog data, and supplies the analog data to the viewing monitor 35 so that the reduced images can be displayed on the viewing monitor 35. At step S70, reduced image display terminates.

Figure 10:
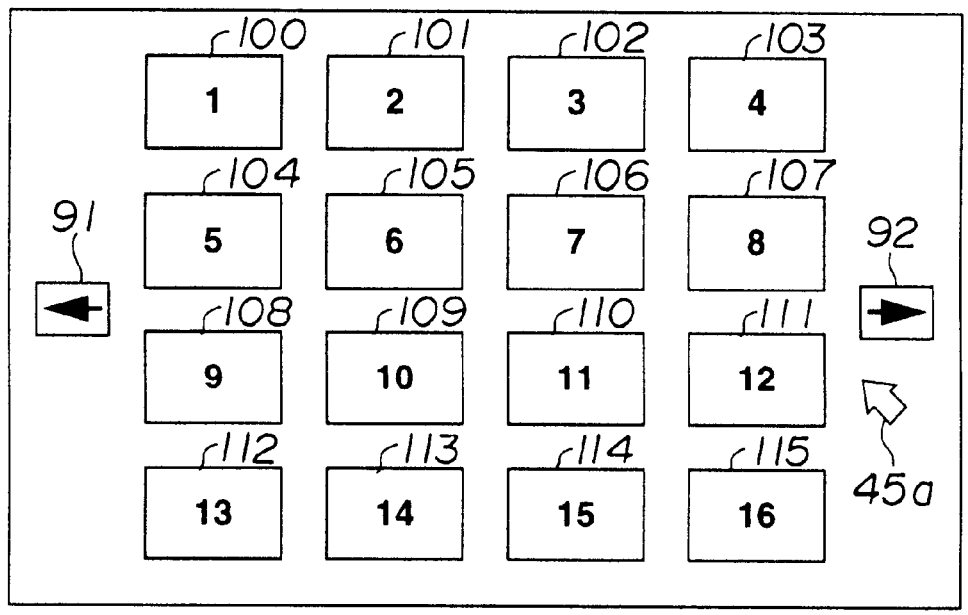

FIG. 10 shows a screen of the retrieval monitor 44 appearing when the number of selected image files is one. Frames 100 to 115 on the retrieval monitor 44 indicate locations of reduced images to be displayed on the viewing monitor 35. In other words, reduced images of endoscopic images are displayed according to the layout shown in FIG. 10 on the viewing monitor 35. Numerals written in the frames 100 to 115 are serial numbers of image files relative to an examination ID number.

Figure 11:
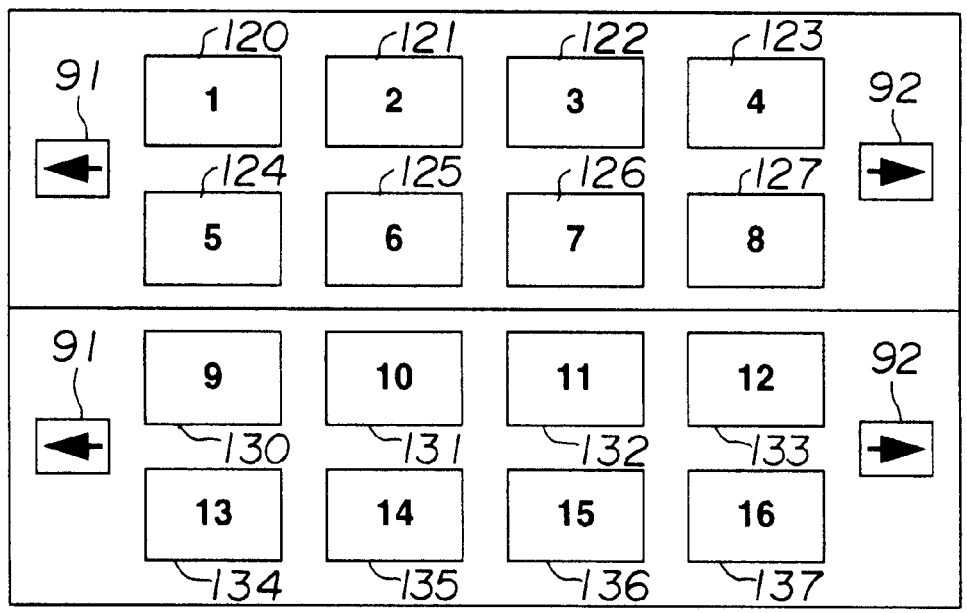

FIG. 11 shows a screen of the retrieval monitor 44 appearing when the number of selected image files is two. Frames 120 to 127 indicate locations of reduced images, which are contained in the first image file retrieved under the first parameters for retrieval, to be displayed on the viewing monitor 35. Frames 130 to 137 indicate locations of reduced images, which are contained in the second image file retrieved under the second parameters for retrieval, to be displayed on the viewing monitor 35. Numerals written in the frames 120 to 127 and 130 to 137 are serial numbers of image files relative to examination ID numbers.

Figure 12:
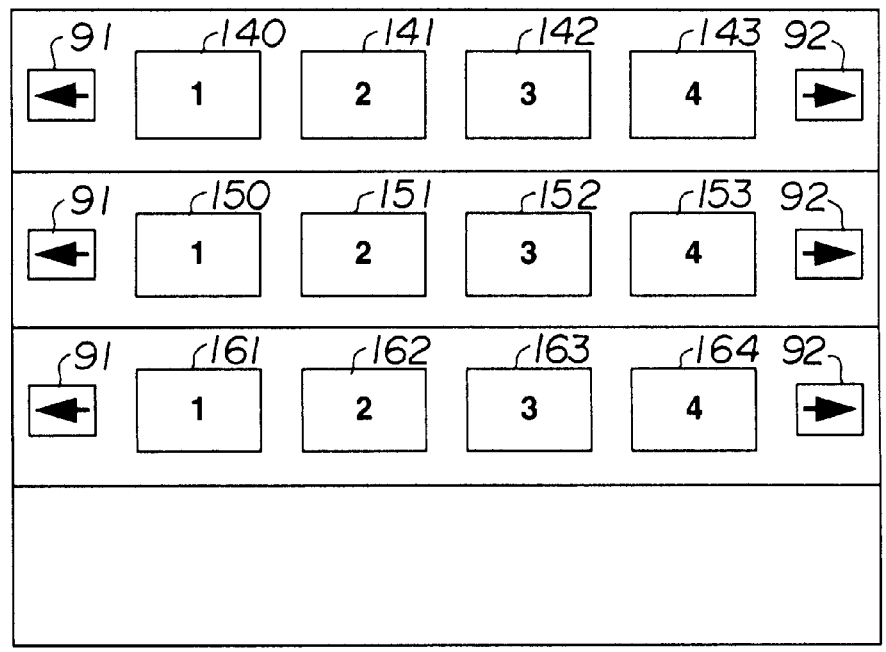

FIG. 12 shows a screen of the retrieval monitor 44 appearing when the number of selected image files is three. Frames 140 to 143 indicate locations of reduced images, which are contained in the first image file retrieved under the first parameters for retrieval, to be displayed on the viewing monitor 35. Frames 150 to 153 indicate locations of reduced images, which are contained in the second image file retrieved under the second parameters for retrieval, to be displayed on the viewing monitor 35. Frames 160 to 163 indicate locations of reduced images, which are contained in the third image file retrieved under the third parameters for retrieval, to be displayed on the viewing monitor 19. Numerals written in the frames 140 to 143, 150 to 153, and 160 to 163 are serial numbers of image files relative to examination ID numbers.

Figure 13:
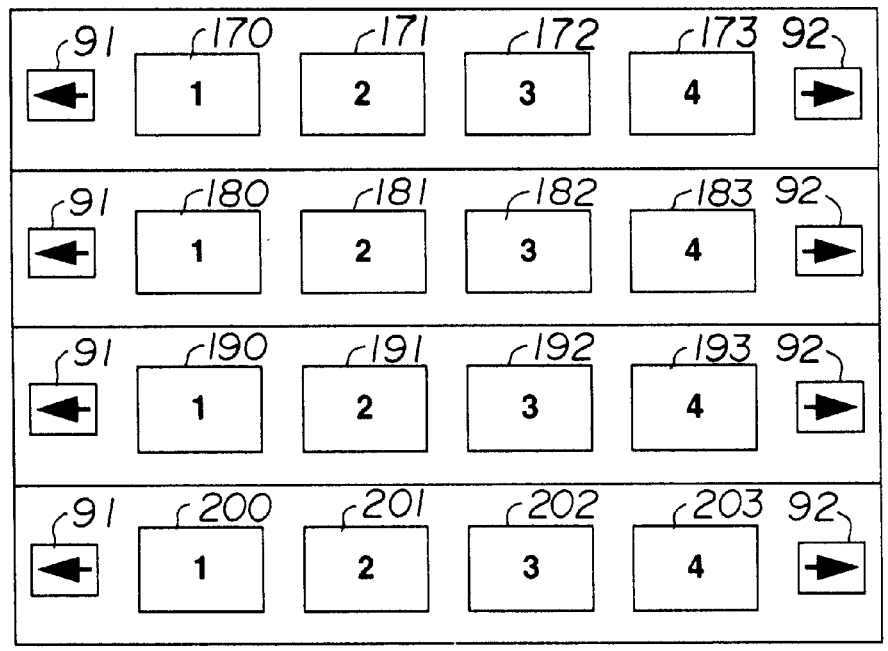

FIG. 13 shows a screen of the retrieval monitor 44 appearing when the number of selected image files is four. Frames 170 to 173 indicate locations of reduced images, which are contained in the first image file retrieved under the first parameters for retrieval, to be displayed on the viewing monitor 35. Frames 180 to 183 indicate locations of reduced images, which are contained in the second image file retrieved under the second parameters for retrieval, to be displayed on the viewing monitor 35. Frames 190 to 193 indicate locations of reduced images, which are contained in the third image file retrieved under the third parameters for retrieval, to be displayed on the viewing monitor 35. Numerals written in the frames 170 to 173, 180 to 183, 190 to 193, and 200 to 203 are serial numbers of image files relative to examination ID numbers.

Next, editing of patient data or examination data will be described.

Figure 14:
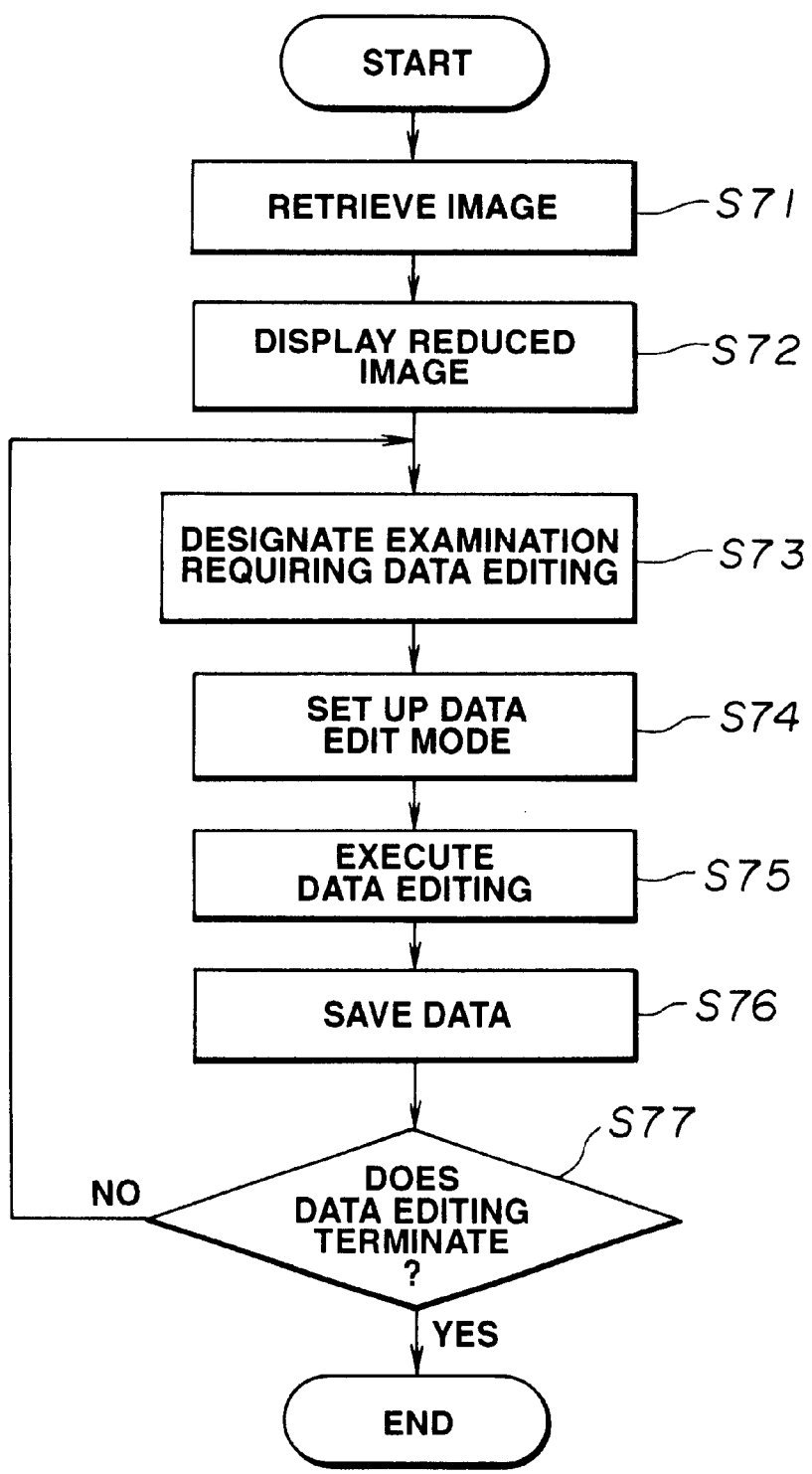

Editing of patient data or examination data is initiated, as shown in FIG. 14, by retrieving image files as described in conjunction with FIG. 7 at step S71 and then displaying reduced images contained in the image files as described in conjunction with FIG. 9 at step S72. FIG. 15 shows a screen of the retrieval monitor 44 appearing when the number of selected image files is four. The screen in FIG. 15 is identical to the one of FIG. 13 except that character data such as a patient ID number, patient name, and date of examination is written by the right side of a reduced-image display area for each set of reduced images. At the corners of character data areas, report display buttons 210 to 213 are depicted so that displaying of detailed data concerning patients in association with respective sets of reduced images can be instructed.

Returning to FIG. 14, description of editing will be continued. When an examination requiring editing of patient data is designated at step S73, any of the report display buttons 210 to 213 shown in FIG. 15 is selected by clicking the mouse 45. Assuming that patient data acquired during three examinations is to be edited, the report display buttons 210, 211, and 213 are activated by clicking the mouse 45. At step S74, patient data edit mode is set up. As shown in FIG. 16, three patient data sets are displayed in the form of windows. The order of displaying the three patient data windows 221, 222, and 223 can be changed by clicking the mouse positioned at a corner of any of the windows. The procedure is identical to the one implemented in a general graphic user interface, of which description will therefore be omitted.

When the edit mode is set up, at step S75 in FIG. 14, patient data written in the patient data windows 221, 222, and 223, for example, findings are edited using the mouse 45 and keyboard 43. When data editing is completed, resultant data is saved on the hard disk 47 at step S76. At step S77, it is waited that an instruction for termination of editing is entered, for example, at the keyboard 42. If editing is continued, control is returned to step S73. If the instruction is entered, editing terminates.

Figure 17:
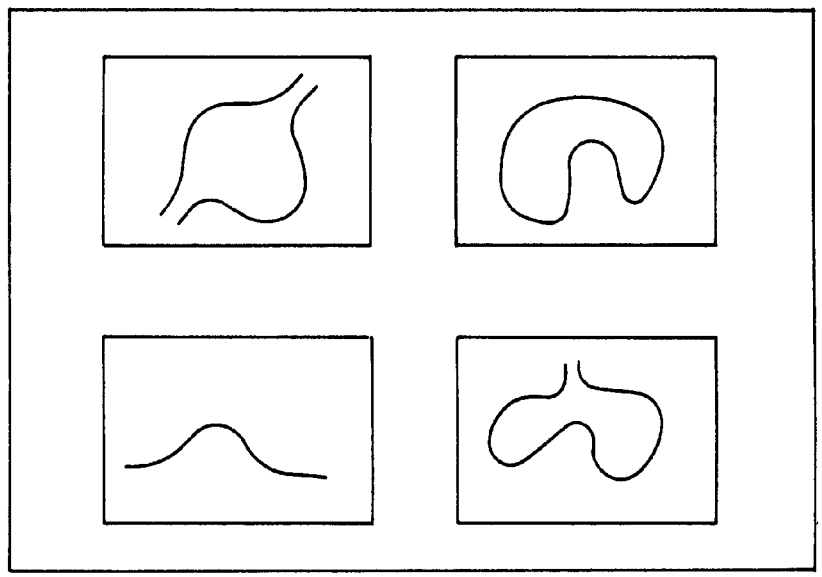

As for a reduced image, a normal image or color view image that is 640 dots wide and 480 dots long may be halved to 320 dots and 240 dots respectively by means of the image processor 32 in the conference unit 6 under the control of the controller 36. Such images may then be displayed in four-division mode on the viewing monitor as shown in FIG. 17.

Figure 18:
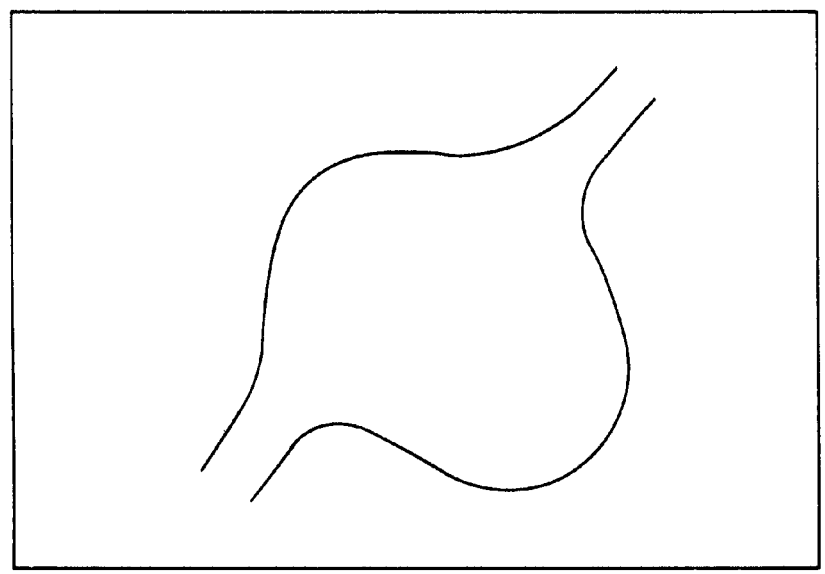

Reduced (index) images appearing on the viewing monitor 35 can be returned to normal images, each of which is 640 dots wide and 480 dots long as shown in FIG. 18, using the mouse 45 or keyboard 42.

Figure 19:
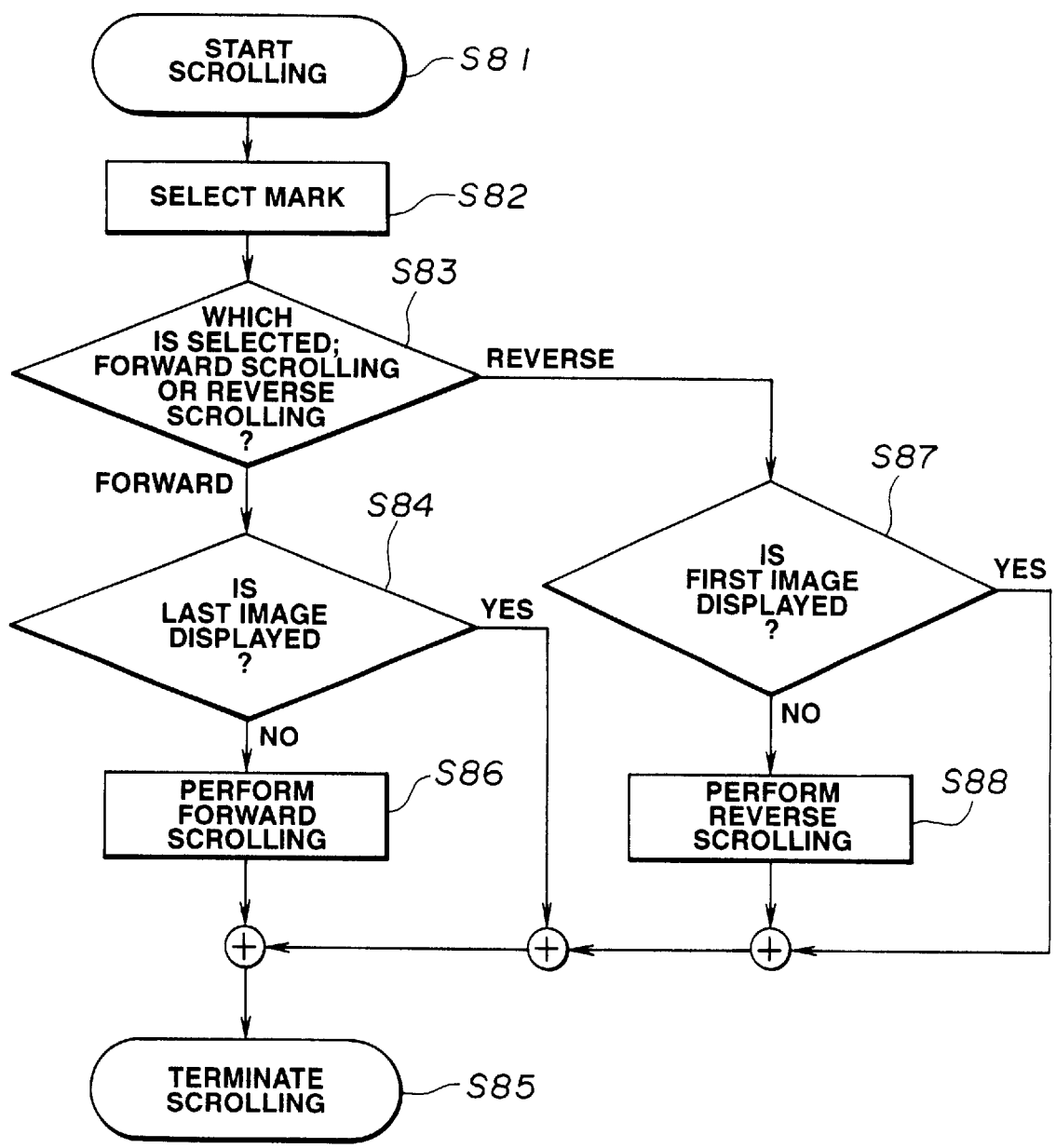

Next, scrolling of a screen showing reduced images contained in selected image files will be described in conjunction with FIG. 19.

Scrolling starts with step S81. At step S82, a left arrow mark 91 or a right arrow mark 92, which is shown in FIG. 10, is selected by the cursor 45a manipulated with the mouse 45. Selected information is placed in the work memory 49.

At step S83, it is determined whether forward or reverse scrolling is selected. When forward scrolling is selected, it is determined at step S84 whether the serial number of a reduced image displayed last is a last number relative to an examination ID number concerned. If the serial number is a last number, scrolling is terminated at step S85. Changing of screens of the retrieval monitor 44 is not carried out. If the serial number is not a last number, reduced images are fed one by one forward or in descending order of serial numbers at step S86.

When reverse scrolling is selected, it is determined at step S87 whether the serial number of a reduced image displayed first is one. If the serial number is one, scrolling is terminated at step S85 and changing of screens of the retrieval monitor 44 is not carried out. If the serial number is not one, reduced images are fed one by one reversely or in ascending order of serial numbers at step S88.

The foregoing scrolling may be performed in units of one line (four images) in FIG. 10, 11, 12, 13, or 15. In FIG. 10, scrolling may be performed in units of one page (sixteen images).

A view image that is provided in the form of digital data by the A/D converter 11 in the input unit in FIG. 1 may be compressed using a DCT or DPCM technique by the image processor 12. In this case, the image processor 32 in the conference unit 6 uses the stretcher 33 to stretch the compressed view image through de-DCT or de-DPCM.

As described so far, according to the image filing system 1 of the present invention, a plurality of reduced (index) images of view images in retrieved image files can be displayed in the same screen so that desired images can be selected easily. Diagnosis can be made as reliably as conventional photograph-dependent diagnosis. A plurality of reduced images contained in image files retrieved according to a plurality of parameters for retrieval can be displayed simultaneously on the viewing monitor 35. This facilitates comparative study of the progress of a patient's disease.

Various instructions can be entered using a mouse. This results in improved operability.

A means for producing view images is not limited to an endoscope system or a diagnostic ultrasound system.

According to the present invention, it will be apparent that a wide range of different embodiments can be formed on the basis of the invention without departing from the spirit or scope of the invention. This invention is limited to the appended claims but not restricted to any specific embodiments.

What is claimed is:

1. A method of managing medical image files, comprising:

an image input step at which image data is inputted;

an image file creating step at which an image file is created by having the image data inputted at said image input step, management information for specifying the image data and reduced image data of said image data respectively be related to one another;

a file storage step at which at least one image file created at said image file creating step is stored in a file storage means;

a retrieving condition input step at which a predetermined retrieving condition to specify desired image data among the image data stored as the image file in said file storage means is inputted;

a retrieving step at which respective management information of the image file stored in said file storage means is retrieved in accordance with the retrieving condition inputted at said retrieving condition input step, and at least one image file is specified based on each of at least one management information which meets said retrieving condition;

a first display control step at which reduced images as many as possible to be displayed in a display area of a display means are displayed on the display means based on the reduced image data of the image file specified at said retrieving step;

a management information display instruction step at which display instruction is given for displaying at least one management information related to the reduced image displayed on the display means at said first display control step;

a management information display instruction reception step at which said display instruction at said management information display instruction step is received when the reduced image based on said reduced image data is displayed on the display means by said first display control step;

a second display control step at which at least one management information instructed to be displayed at said management information display instruction step is displayed on a display means when said display instruction is received at said management information display instruction reception step;

a scrolling instruction step at which instruction is given to perform a scrolling to display reduced image, which is related to the reduced image displayed on the display means by said first display control step but not displayed on the display means on the display means; and a scrolling step at which a scrolling is performed to display the reduced image which is related to the reduced image displayed on the display means by said first display control step but not displayed on the display means, on the display means upon scrolling display instruction by said scrolling instruction means.

2. A method of managing medical image files according to claim 1, further comprising:

a selecting step at which any desired management information of the management information displayed on the display means at said second display control step is selected; and an editing step at which the management information selected at said selecting step is edited.

3. A method of managing medical image files, comprising:

an image input step at which image data is inputted;

an image file creating step at which an image file is created by having the image data inputted at said image input step, management information for specifying the image data and reduced image data of said image data respectively be related to one another;

a file storage step at which at least one image file created at said image file creating step is stored in a file storage means;

a retrieving condition input step at which a predetermined retrieving condition to specify desired image data among the image data stored as the image file in said file storage means is inputted;

a retrieving step at which respective management information of the image file stored in said file storage means is retrieved in accordance with the retrieving condition inputted at said retrieving condition input step, and at least one image tile is specified based on each of at least one management information which meets said retrieving condition;

a first display control step at which at least one reduced image is displayed on a display means based on the reduced image data of the image file specified at said retrieving step;

a management information display instruction step at which display instruction is given for displaying at least one management information related to the reduced image displayed on the display means by said first display control step;

a management information display instruction reception step at which said display instruction at said management information display instruction step is received when the reduced image based on said reduced image data is displayed on the display means by said first display control step; and a second display control step at which at least one management information instructed to be displayed at said management information display instruction step is displayed on the display means when said display instruction is received at said management information display instruction reception step.

4. A method of managing medical image files according to claim 3, further comprising a data memory step at which at least images contained in said image files retrieved at said file retrieval step are temporarily stored.

5. A method of managing medical image files according to claim 3 or 4, further comprising a display control step at which a screen provided at said display step is controlled according to the number of image files selected at said selection step.

6. A method of managing medical image files according to claim 3 or 4, wherein said image is an endoscopic image.

7. A method of managing medical image files according to claim 3, further comprising:

a selecting step at which any desired management information of the management information displayed on the display means at said second display control step is selected; and an editing step at which the management information selected at said selecting step is edited.

8. A medical image file system, comprising;

an image input means for inputting image data;

an image file creating means for creating an image file by having the image data inputted by said image input means, management information for specifying said image data and reduced image data of said image data respectively be related to one another;

a file storage means for storing at least one image file created by said image file creating means;

a retrieving condition input means for inputting a predetermined retrieving condition to specify desired image data among the image data stored as the image file in said file storage means;

a retrieving means for retrieving respective management information of the image file stored in said file storage means in accordance with the retrieving condition inputted by said retrieving condition input means and specifying at least one image file based on each of at least one management information which meets said retrieving condition;

a first display control means for displaying reduced images as many as possible to be displayed in a display area of a display means on the display means based on the reduced image data of the image file specified by said retrieving means;

a management information display instruction means for instructing to display at least one management information related to the reduced image displayed by said first display control means on the display means;

a management information display instruction reception means for receiving said display instruction from said management information display instruction means when the reduced image based on said reduced image data is displayed on the display means by said first display control means;

a second display control means for displaying at least one management information instructed to be displayed by said management information display instruction means on the display means when said display instruction is received by said management information display instruction reception means;

a scrolling instruction means for instructing to perform a scrolling to display reduced image, which is related to the reduced image displayed on the display means by said first display control means but not displayed on the display means on the display means; and a scrolling means for performing a scrolling to display the reduced image, which is related to the reduced image displayed on the display means by said first display control means but not displayed on the display means on the display means upon scrolling display instruction by sad scrolling instruction means.

9. A medical image filing system according to claim 8, further comprising:

a selecting means for selecting any desired management information of the management information displayed on the display means by said second display control means; and an editing means for editing the management information selected by said selecting means.

10. A medical image filing system, comprising:

an image input means for inputting image data;

an image file creating means for creating an image file by having the image data inputted by said image input means, management information for specifying the image data and reduced image data of said image data respectively be related to one another;

a file storage means for storing at least one image file created by said image file creating means;

a retrieving condition input means for inputting a predetermined retrieving condition to specify desired image data among the image data stored as the image file in said file storage means;

a retrieving means for retrieving respective management information of the image file stored in said file storage means in accordance with the retrieving condition inputted by said retrieving condition input means and specifying at least one image file based on each of at least one management information which meets said retrieving condition;

a first display control means for displaying at least one reduced image on a display means based on the reduced image data of the image file specified by said retrieving means;

a management information display instruction means for instructing to display at least one management information related to the reduced image displayed on the display means by said first display control means on the display means;

a management information display instruction reception means for receiving said display instruction from said management information display instruction means when the reduced image based on said reduced image data is displayed on the display means by said first display control means; and a second display control means for displaying on the display means at least one management information instructed to be displayed by said management information display instruction means when said display instruction is received by said management information display instruction reception means.

11. A medical image filing system according to claim 10, further comprising a data memory means for temporarily storing at least said images fetched from said image files retrieved by said file retrieving means.

12. A medical image filing system according to claim 10, further comprising a display control means for controlling said display means according to the number of image files selected by said selecting means.

13. A medical image filing system according to claim 12, further comprising:

a password input means for inputting a password;

a password memory means for storing said password;

a password supervising means for supervising said password stored in said password memory means; and a control means for controlling said retrieving means according to a result of supervision made by said password supervising means.

14. A medical image filing system according to claim 12 further comprising:

a keyhole means into which a key is fitted in order to close a lock;

a key and lock supervising means for supervising the state in which said lock is closed with said key; and a control means for controlling said retrieving means according to a result of supervision made by said key and lock supervising means.

15. A medical image filing system according to claim 12, further comprising:

an image compressing means for compressing said image file on a reversible or non-reversible basis so as to produce a compressed image file; and an image stretching means for stretching said compressed image file;

said file storage means storing a compressed image file, and said display means displaying an image contained in said compressed image file stretched by said image stretching means.

16. A medical image filing system according to claim 12, wherein said image is an endoscopic image.

17. A medical image filing system according to claim 10, further comprising an information display means for displaying said management information concerning said plurality of reduced images displayed by said display means at a position associated with the position at which said plurality of reduced images are displayed.

18. A medical image filing system according to claim 17, further comprising a reduced image selecting means that when the number of reduced images contained in each image file exceeds the number of reduced images which can be displayed by said display means, modifies said management information to be displayed by said information display means and selects reduced images to be displayed by said display means.

19. A medical image filing system according to claim 10 or 11, further comprising:

a password input means for inputting a password;

a password memory means for storing said password;

a password supervising means for supervising said password stored in said password memory means; and a control means for controlling said retrieving means according to a result of supervision made by said password supervising means.

20. A medical image filing system according to claim 10 or 11, further comprising:

a keyhole means into which a key is fitted in order to close a lock;

a key and lock supervising means for supervising the state in which said lock is closed with said key; and a control means for controlling said retrieving means according to a result of supervision made by said key and lock supervising means.

21. A medical image filing system according to claim 10 or 11 further comprising:

an image compressing means for compressing said image file on a reversible or non-reversible basis so as to produce a compressed image file; and an image stretching means for stretching said compressed image file;

said file storage means storing a compressed image file, and said display means displaying an image contained in said compressed image file stretched by said image stretching means.

22. A medical image filing system according to claim 10 or 11, wherein said image is an endoscopic image.

23. A medical image filing system according to claim 10, further comprising:

a selecting means for selecting any desired management information of the management information displayed on the display means by said second display control means; and an editing means for editing the management information selected by said selecting means.

* * * * *